United States Patent [19]

Inoue et al.

[11] 4,197,166

[45] Apr. 8, 1980

[54] DEHYDRATING PURIFICATION PROCESS FOR A FERMENTATION PRODUCT

[75] Inventors: Shigeo Inoue, Saitama; Yoshiharu Kimura, Funabashi; Manzo Kinta, Funaba, all of Japan

[73] Assignee: Kao Soap Company, Limited, Tokyo, Japan

[21] Appl. No.: 928,964

[22] Filed: Jul. 28, 1978

[30] Foreign Application Priority Data

Aug. 1, 1977 [JP] Japan ............................ 52-92428

[51] Int. Cl.$^2$ .............................................. B01D 3/34
[52] U.S. Cl. .................................. 203/14; 203/64; 203/91; 435/74; 435/803; 435/944; 536/4; 536/116; 536/119
[58] Field of Search ................ 203/14, 18, 91, 64; 195/31 R, 82; 536/4, 116, 119

[56] References Cited

U.S. PATENT DOCUMENTS 3,378,542  4/1968  O'Boyle ............................ 536/4

OTHER PUBLICATIONS

J. F. T. Spencer et al., Canadian Journal of Chemistry, 39, 846 (1961).

Tulloch et al., Journal of Organic Chemistry, vol. 37, No. 18, 1972 (2868-2870).

Primary Examiner—Wilbur L. Bascomb, Jr.
Attorney, Agent, or Firm—Oblon, Fisher, Spivak, McClelland & Maier

[57] ABSTRACT

A dehydrating purification process for a fermentation product, which comprises adding at least one polyhydric alcohol represented by the formulae (III) or (IV),

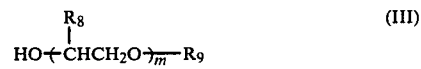

or

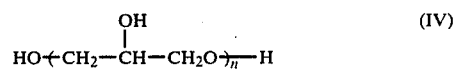

wherein $R_8$ represents a hydrogen atom or a methyl group, $R_9$ represents a hydrogen atom or an alkyl group having 1 to 5 carbon atoms, and m and n represent integers from 1 to 6, to hydrated Sophorolipid or a secondary derivative thereof which is a fermentation product of Torulopsis bombicola, and distilling off water with heating under reduced pressure.

5 Claims, No Drawings

DEHYDRATING PURIFICATION PROCESS FOR A FERMENTATION PRODUCT

BACKGROUND OF THE INVENTION

1. Field of the Invention

This invention relates to a dehydrating purification process for a fermentation product, more particularly to a purification process for producing Sophorolipid or a secondary derivative thereof having a lower viscosity, which comprises purifying by dehydration Sophorolipid or a secondary derivative thereof which is a fermentation product of Torulopsis bombicola.

2. Description of the Prior Art

It has been reported by J. F. T. Spencer et al. [Canadian Journal of Chemistry, 39, 846 (1961)] that a great quantity of Sophorolipid is produced in a fermentation liquid by culturing Torulopsis bombicola.

Sophorolipid is considered to be a mixture of the compounds represented by the formulae (I) and (II),

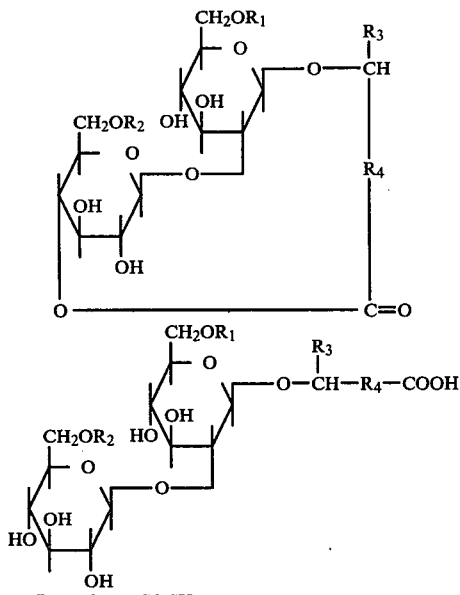

I - a : $R_1 = R_2 = COCH_3$
I - b : $R_1 = COCH_3, R_2 = H$
I - c : $R_1 = H, R_2 = COCH_3$
I - d : $R_1 = R_2 = H$
II - a : $R_1 = R_2 = COCH_3$
II - b : $R_1 = COCH_3, R_2 = H$
II - c : $R_1 = H, R_2 = COCH_3$
II - d : $R_1 = R_2 = H$ wherein $R_3$ represents a hydrogen atom or a methyl group, and $R_4$ represents a saturated or unsaturated hydrocarbon group having 12 to 16 carbon atoms when $R_3$ is a hydrogen atom, and $R_4$ represents a saturated or unsaturated hydrocarbon group having 11 to 15 carbon atoms when $R_3$ is a methyl group.

These compounds are useful as cleansers and emulsifiers having both excellent hygroscopic and hydrophilic properties due to their Sophorose groups and hydrophobic properties arising from the fatty acid. Particularly, the hygroscopic property due to the Sophorose group and the cleansing ability arising from the fatty acid provide a wetting agent with excellent properties which in addition support skin physiology.

However, Sophorolipid is an aggregate of many homologs. For instance, when fermented with an octadecane as a source of hydrocarbon, there is produced about 40% of (I-a), about 8% of (I-b) and (I-c), about 30% of (II-a), about 6% of (II-b) and (II-c), about 14% of an isomer resulting from the position of the lactone bond, and small amount of (I-d) and (II-d). The formation ratio of these homologs varies depending on the hydrocarbon source and fermentation conditions.

As can be seen from the above structures, the compounds of the formula (I) differ from those of the formula (II) in the bonding of the fatty acid moiety. Consequently, the number of hydroxy groups in the Sophorose group and the acetyl values of the homologs are different from each other. These structural differences result in diversified physicochemical properties. Namely, the solubility in organic solvents and water and the surface-active properties vary, depending on the structure. For instance, the compound of the formula (I-a) possesses an oily property, and is readily soluble in water, and the compounds of the formulae (I-b) and (I-c) have emulsifying characteristics to some extent. The compound of the formula (I-d) is readily soluble in water and has a cleansing ability with a rather high HLB value. The compound of the formula (II-a) is emulsified and dispersed in water and acts as an excellent emulsifier. The compounds of the formulae (II-b) and (II-c) are readily soluble in water and possess a cleansing ability and foaming properties. The compound of the formula (II-d) remarkably functions as a cleanser having an HLB value of 30 to 40, which value is not less than those of anionic surface active and a non-ionic cleansers.

Therefore, it should be noted that the properties and functions vary with the ratios of those homologs because the mixture of the homologs is actually used. Further, difficulty is encountered in that a desired product having a given ratio of the homologs must be produced by fermentation.

The acetyl and lactone bonds in Sophorolipid are chemically unstable and easily cleaved under weakly alkaline conditions (pH 9–10) at room temperature. This cleavage is promoted also under mineral acid conditions. Even in the vicinity of neutrality, both bonds are gradually hydrolyzed by heating or during prolonged storage of Sophorolipid so that Sophorolipid is finally converted into the compound of the formula (II-d).

However, the principal carbon skeleton of Sophorolipid is a L-[(2′-O-β-D-glucopyranosyl-β-D-glucopyranosyl)-oxy]alkane acid or alkene acid which is formed by combining Sophorose with a hydroxyfatty acid via a glycosyl ether bond and is chemically stable.

Consequently, various secondary derivatives of Sophorolipid have been produced which are of good and stable quality and performance. Some typical compounds of these derivatives are as follows:

(V)

structure with $R_3$, $R_4$—COOR$_5$

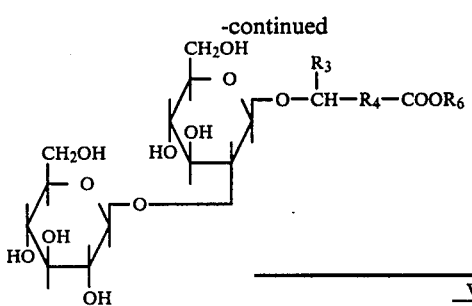

(VI)

dehydrating agent, the secondary derivatives cannot be prepared in an ethyl acetate solvent system since the solvent itself acts as a reacting substrate. Therefore, the solvent must be exhaustively distilled off.

However, exhaustive elimination of the water or solvent is nearly impossible from an industrial standpoint because Sophorolipid and secondary derivatives thereof are extremely viscous substances as shown in Table 1.

Table 1

| | Viscosity of Sophorolipid and secondary derivatives thereof | | | | | | |
|---|---|---|---|---|---|---|---|
| | Sophorolipid | | | Secondary derivatives | | | |
| Temperature (°C.) | Water content 14.1% | Water content 5.3% | Water content 0.4% | Compound (II - d) | Compound (V) ($R_5 = CH_3$) | Compound (VI) ($R_6 = C_{18}H_{35}$) | Compound (VII) ($R_7 = CH_3$, $CH_2CHOH$) |
| 20 | >100,000 | >100,000 | >100,000 | >100,000 | >100,000 | >100,000 | >100,000 |
| 60 | 320 | 1,900 | (65° C.) 63,000 | >100,000 | >100,000 | >100,000 | 4,300 |
| 80 | 150 | 1,350 | 20,000 | >100,000 | 38,000 | 12,000 | 1,400 |

Note:
The numerical values indicate viscosities (cps) measured with a B type viscosimeter made by Tokyo Keiki Co., Ltd.

(VII)

wherein $R_5$ represents a hydrogen atom or a methyl group, $R_6$ represents an alkyl group having 2 to 20 carbon atoms, $R_7$ represents a hydroxyalkyl group having 2 to 5 carbon atoms, and $R_3$ and $R_4$ are the same as defined above.

These secondary derivatives are stable and have surmounted the above noted defects. However, the production of these derivatives involves various problems. That is, only Sophorolipid having a water content of 40 to 50% is obtained from the fermentation liquid by decantation. The existence of water inhibits the reaction, prevents Sophorolipid from conversion into secondary derivatives and causes by-products. For instance, when Sophorolipid is subjected to a methanolysis reaction with an acid catalyst in the presence of water in order to obtain the compound of the formula (V), only a mixture of the compounds of the formulae (V) and (II-d) is produced, and no single substance can be obtained.

With the exception of ethyl acetate, there have been found no solvents which can extract Sophorolipid efficiently from a Sophorolipid solution obtained from the fermentation liquid or by any slant method because Sophorolipid is an aggregate of many homologs which are very different in their solubilities in organic solvents.

Ethyl acetate allows for the recovery of at most 80% but is indispensably coexistent with water by reason of the fact that ethyl acetate itself contains 5 to 10% of water. Even if the existing water is eliminated with a In view of these difficulties, the present inventors have made continued studies on the lowering of viscosities of Sophorolipid and secondary derivatives thereof. Substances to be added for this purpose should preferably have the following properties:

1. Good miscibility with Sophorolipid or secondary derivatives thereof.
2. Liquid form at room temperature.
3. Significant decrease in viscosity by addition of only a small amount.
4. Higher boiling point than water.
5. Not reactive or less reactive than reaction agents.
6. Do not interfere with the properties of a desired product even if reactive.
7. Safety to human bodies and others.

The present inventors have examined a wide variety of substances, and as a result, have found that polyhydric alcohols meet with the above desired properties and give the best results. Based on this finding, this invention has been accomplished.

SUMMARY OF THE INVENTION

This invention provides a dehydrating purification process for a fermentation product, which comprises adding at least one polyhydric alcohol represented by the formula (III) or (IV) to hydrated Sophorolipid or a secondary derivative thereof which is a fermentation product of Torulopsis bombicola, distilling off water with heating under reduced pressure, and obtaining a solution of Sophorolipid or a secondary derivative thereof having a lowered viscosity.

DETAILED DESCRIPTION OF THE PREFERRED EMBODIMENTS

Suitable polyhydric alcohols which are useful in the invention are represented by the formula (III) or (IV),

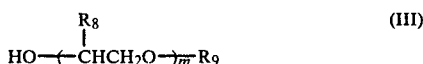

(III)

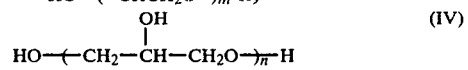

(IV)

wherein $R_8$ represents a hydrogen atom or a methyl group, $R_9$ represents a hydrogen atom or an alkyl group having 1 to 5 carbon atoms, and m and n represent integers from 1 to 6.

The polyhydric alcohols includes, for example, ethylene glycol, ethylene glycol monomethyl ether, ethylene glycol monoethyl ether, ethylene glycol monopropyl ether, diethylene glycol, diethylene glycol monomethyl ether, diethylene glycol monoethyl ether, diethylene glycol monobutyl ether, polyethylene glycol having an average molecular weight less than 300, propylene glycol, dipropylene glycol, tripropylene glycol, tetrapropylene glycol, pentapropylene glycol, hexapropylene glycol, propylene glycol monomethyl ether, propylene glycol monoethyl ether, propylene glycol monobutyl ether, dipropylene glycol monomethyl ether, dipropylene glycol monoethyl ether, tripropylene glycol monomethyl ether, block copolymers of ethylene glycol and propylene glycol having an average molecular weight of less than 360 and the like as represented by the formula (III), and, for example, glycerine, polyglycerine and the like as represented by the formula (IV).

These polyhydric alcohols possess good miscibility with Sophorolipid and secondary derivatives thereof. Addition of these alcohols causes a significant decrease in the viscosities of Sophorolipid and derivatives thereof as shown in Table 2.

Any one of the alcohols sufficiently decreases the viscosities of Sophorolipid and its derivatives in an amount of 1 or more percent by weight. The maximum amount is not specifically limited, but 1 to 10 percent by weight is particularly preferable.

In carrying out the present invention, to hydrated Sophorolipid or a secondary derivative thereof is first added at least one polyhydric alcohol, and then water is exhaustively distilled under reduced pressure with the use of any conventional topping apparatus. On this occasion, any impurities having an offensive smell and a lower boiling point which are contained in the raw material are distilled off.

The thus obtained polyhydric alcohol solution of Sophorolipid or its secondary derivatives is completely free of water and is extremely low in viscosity. Consequently, this solution is useful in producing other desirable derivatives. For instance, a hydroxyfatty acid polyhydric alcohol ester, which is employed as a raw material for a large ring lactone musk as a perfume, is easily obtained through alcoholysis by adding an acid catalyst to the polyhydric alcohol solution of Sophorolipid.

The invention will now be described in further detail with reference to a non-limiting Example.

EXAMPLE 1

(1) To a mixture of 1500 g of glucose, 75 g of a yeast extract and 15 g of urea was added water to adjust the whole volume to 15 l, and the resulting mixture was sterilized and utilized as a fermentation liquid. To this fermentation liquid was inoculated Torulopsis bombicola which had been cultured on the slant in a YM agar culture medium, and the mixture was fermented at 20° C. with stirring at a speed of 300 rpm and at an aeration of 0.33 VVM. The mixture was cultured for 24 hours after inoculation, and to this mixture was added 10 g/l of octadecane. Thereafter, the octadecane was added in the above ratio at intervals of 24 hours up to a total amount of 900 g. After the final addition of octadecane, the mixture was fermented for 24 hours. The fermentation time totalled 168 hours. A Sophorolipid layer which precipitated at the bottom of the fermentor was collected by decantation to give 1800 g of Sophorolipid or its derivatives having a viscosity of about 1500 cps at 30° C. and containing 45% of water.

(2) 70 g of the thus obtained Sophorolipid was placed in a 100 ml round bottom flask equipped with a stirrer and a Liebig condenser. The mixture was evaporated with stirring at 80° C. in an oil bath under a reduced pressure of 250 mmHg to eliminate water. On the other hand, to Sophorolipid or its derivative was added any one of the polyhydric alcohols listed in Table 2 in a ratio of 5.0% or 10.0% by weight, and the same procedure as above was repeated to eliminate water.

In the case of Sophorolipid only, the viscosity increased as the water was evaporated, and stirring became impossible when the water content became less than 5%. At this time, Sophorolipid could not be taken out of the container. On the contrary, in the case where the polyhydric alcohol was added, the water content was found to be 0.4 to 0.6% (measured by Karl Fischer's method) after a lapse of about 120 minutes. In any case, good fluidity was observed. These viscosities were measured by a B type viscosimeter at 80° C., and the results obtained are as shown in Table 2.

The compounds of the formulae (V), (VI) and (VII) were prepared as follows:

(a) Preparation of the compound (V)

To 50 g of the Sophorolipid sample thus obtained which was made by adding the polyhydric alcohol were added 350 g of methanol and then sulfuric acid. The mixture was reacted at 40° to 43° C. for about 60 minutes. After completion of the reaction, the mixture was neutralized with potassium hydroxide, and the precipitated potassium sulfate was removed by filtration.

(b) Preparation of the Compound (VI)

To the sample obtained by the process (a) were added oleyl alcohol and then a methanol solution of potassium hydroxide to prepare homogeneous solution, which was subjected to an ester interchange reaction at 60° C./150 to 500 mmHg with the use of a thin film type molecular still to obtain the compound of the formula (VI).

(c) Preparation of the compound (VII)

To the compound (V) were added water and ethanol and then potassium hydroxide, and the resulting mixture was refluxed to hydrolyze the compound (V), and the ethanol and formed methanol were distilled away. Then, the water was distilled off at 60° C./70 to 100 mmHg to obtain the potassium salt of (II-d). To this salt was added a given amount of propylene oxide, and the resulting mixture was reacted with heating to obtain the compound (VII).

Table 2

| Polyhydric alcohol | Viscosity (cps 80° C.) | | | | | | | | | |
| --- | --- | --- | --- | --- | --- | --- | --- | --- | --- | --- |
| | 2.5% by weight addition | | | | | 5.0% by weight addition | | | | |
| | SL | II-d | V | VI | VII | SL | II-d | V | VI | VII |
| Ethylene glycol | A | A | A | A | A | A | A | A | A | A |
| Ethylene glycol monomethyl ether | A | B | B | A | A | A | A | A | A | A |
| Ethylene glycol monoethyl ether | A | B | B | A | A | A | A | A | A | A |

Table 2-continued

| Polyhydric alcohol | Viscosity (cps 80° C.) | | | | | | | | | |
|---|---|---|---|---|---|---|---|---|---|---|
| | 2.5% by weight addition | | | | | 5.0% by weight addition | | | | |
| | SL | II-d | V | VI | VII | SL | II-d | V | VI | VII |
| Ethylene glycol monopropyl ether | B | B | B | A | A | A | B | B | A | A |
| Diethylene glycol | A | A | A | A | A | A | A | A | A | A |
| Diethylene glycol monomethyl ether | A | B | B | A | A | A | A | A | A | A |
| Diethylene glycol monoethyl ether | A | B | B | B | A | A | A | A | A | A |
| Diethylene glycol monobutyl ether | B | B | B | A | A | A | B | B | A | A |
| Polyethylene glycol (Molecular weight 150) | A | B | B | A | A | A | A | A | A | A |
| Polyethylene glycol (Molecular weight 280) | C | C | C | B | A | B | B | B | A | A |
| Propylene glycol | B | C | B | B | A | A | A | A | A | A |
| Propylene glycol monomethyl ether | C | D | C | C | A | A | B | B | A | A |
| Propylene glycol monoethyl ether | C | D | C | C | A | A | B | B | A | A |
| Propylene glycol monobutyl ether | C | D | C | C | A | A | B | B | A | A |
| Dipropylene glycol | A | B | A | A | A | A | A | A | A | A |
| Dipropylene glycol monomethyl ether | A | B | A | A | A | A | A | A | A | A |
| Dipropylene glycol monoethyl ether | A | B | B | A | A | A | A | A | A | A |
| Tripropylene glycol | B | C | B | A | A | A | B | A | A | A |
| Polypropylene glycol (Molecular weight 200) | B | C | B | A | A | A | A | A | A | A |
| Polypropylene glycol (Molecular weight 400) | C | D | D | B | A | B | C | B | B | A |
| Polypropylene glycol (Molecular weight 600) | D | D | D | C | B | B | C | C | A | A |
| Glycerine | C | D | C | B | A | B | C | B | A | A |
| Polyglycerine | C | D | C | B | A | B | C | B | A | A |
| Ethylene glycol mono-2'-hydroxypropyl ether | A | A | A | A | A | A | A | A | A | A |
| Ethylene glycol. Propylene glycol block-polymer (Molecular weight 240) | A | B | A | A | A | A | A | A | A | A |
| Ethylene glycol.Propylene glycol block-polymer (Molecular weight 480) | B | B | B | A | A | A | A | A | A | A |

Note 1 : SL indicates Sophorolipid obtained in (1).
Note 2 : Indications of viscosities
A : <500 cps
B : 500 ~ 1,000 cps
C : 1,000 ~ 2,500 cps
D : 2,500 ~ 5,000 cps

What is claimed is:

1. A dehydrating purification process for a fermentation product, which comprises adding at least one polyhydric alcohol represented by the formulae (III) or (IV),

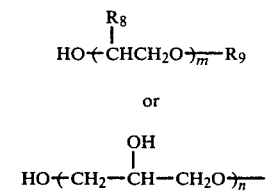

wherein $R_8$ represents a hydrogen atom or a methyl group, $R_9$ represents a hydrogen atom or an alkyl group having 1 to 5 carbon atoms, and m and n represent integers from 1 to 6, to hydrated Sophorolipid or a secondary derivative thereof which is a fermentation product of Torulopsis bombicola, and distilling off water with heating under reduced pressure.

2. A dehydrating purification process according to claim 1, wherein said Sophorolipid is a mixture of the compounds represented by the formulae (I) and (II),

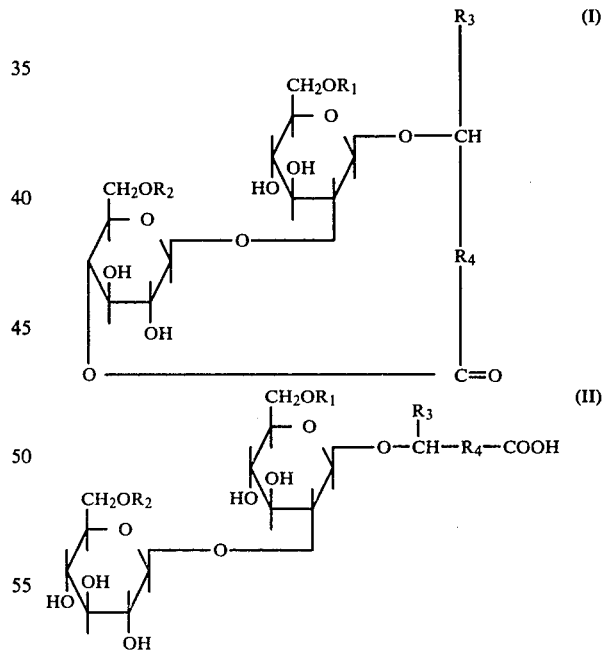

I-a : $R_1 = R_2 = COCH_3$
I-b : $R_1 = COCH_3, R_2 = H$
I-c : $R_1 = H, R_2 = COCH_3$
I-d : $R_1 = R_2 = H$
II-a : $R_1 = R_2 = COCH_3$
II-b : $R_1 = COCH_3, R_2 = H$
II-c : $R_1 = H, R_2 = COCH_3$
II-d : $R_1 = R_2 = H$ wherein $R_3$ represents a hydrogen atom or a methyl group, $R_4$ represents a saturated or unsaturated hydrocarbonyl group having 12 to 16 carbon atoms when $R_3$ is a hydrogen atom, and $R_4$ represents a saturated or unsaturated hydrocarbonyl group having 11 to 15 carbon atoms when $R_3$ is a methyl group.

3. A dehydrating purification process according to claim 1, wherein said secondary derivative Sophorolipid is selected from the group consisting of the compounds represented by the formulae (V), (VI) and (VII)

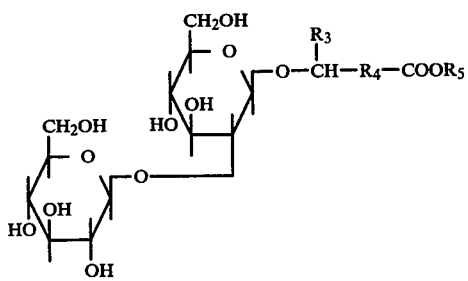
(V)

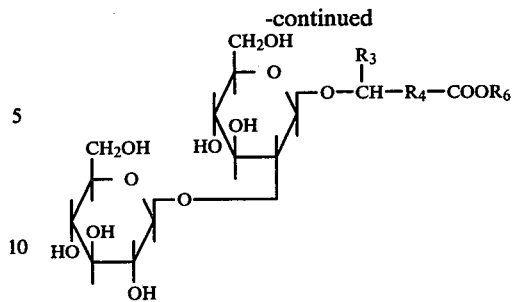
(VI)

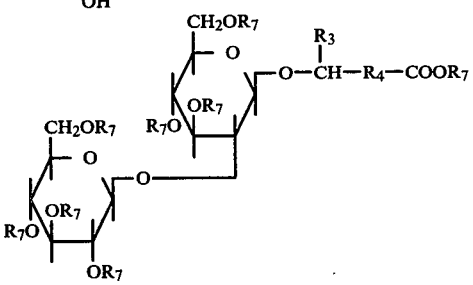
(VII)

wherein $R_5$ is a hydrogen atom or a methyl group, $R_6$ represents an alkyl group having 2 to 20 carbon atoms, $R_7$ represents a hydroxyalkyl group having 2 to 5 carbon atoms, $R_3$ represents a saturated or unsaturated hydrocarbon group having 12 to 16 carbon atoms when $R_3$ is a hydrogen atom, and $R_4$ represents a saturated or unsaturated hydrocarbon group having 11 to 15 carbon atoms when $R_3$ is a methyl group.

4. A dehydrating purification process according to any one of claims 1 to 3, wherein $R_8$ and $R_9$ represent a hydrogen atom or a methyl group, and m is an integer from 1 to 3 in the formula (III).

5. A dehydrating purification process according to claim 1, wherein said polyhydric alcohol is added in an amount of 1 to 10% by weight.

* * * * *